(12) United States Patent
Metzger et al.

(10) Patent No.: US 7,165,860 B1
(45) Date of Patent: Jan. 23, 2007

(54) VIEWING APPARATUS

(75) Inventors: Karen Lee Metzger, Falmouth, ME (US); Kathryn L. Mullins, Cape Neddick, ME (US); Lisa J. Paquet, Biddeford, ME (US)

(73) Assignee: Precision Medical Technology, LLC, Cape Neddick, ME (US)

( * ) Notice: Subject to any disclaimer, the term of this patent is extended or adjusted under 35 U.S.C. 154(b) by 169 days.

(21) Appl. No.: 10/715,909

(22) Filed: Nov. 18, 2003

Related U.S. Application Data (60) Provisional application No. 60/427,432, filed on Nov. 19, 2002.

(51) Int. Cl.
  *F21V 33/00* (2006.01)
(52) U.S. Cl. ...................................... 362/143; 362/259
(58) Field of Classification Search ................ 362/135, 362/138, 139, 140, 141, 142, 143, 144, 259
  See application file for complete search history.

(56) References Cited

U.S. PATENT DOCUMENTS

| | | | |
|---|---|---|---|
| 1,220,069 A | | 3/1917 | Capdevila |
| 1,350,042 A | * | 8/1920 | Stealy .......................... 362/139 |
| 2,017,472 A | | 10/1935 | Re |
| D160,995 S | | 11/1950 | Busa |
| 4,161,955 A | | 7/1979 | Webb |
| 4,339,104 A | | 7/1982 | Weidman |
| 4,966,450 A | * | 10/1990 | Mori ........................... 362/139 |
| D316,635 S | | 5/1991 | Smith |
| 5,012,852 A | | 5/1991 | Blackhurst |
| 5,359,461 A | | 10/1994 | Rice et al. |
| 5,453,915 A | * | 9/1995 | Bradley, III ................ 362/135 |
| 5,604,633 A | | 2/1997 | Christianson |
| D416,691 S | | 11/1999 | Logan, Jr. |
| D438,389 S | | 3/2001 | Ross et al. |
| D444,634 S | | 7/2001 | Dodson |
| 6,305,810 B1 | * | 10/2001 | Mercado ..................... 362/144 |
| 6,382,802 B1 | | 5/2002 | Goodman |

\* cited by examiner

*Primary Examiner*—Y. My Quach-Lee
(74) *Attorney, Agent, or Firm*—Patricia M. Mathers; Thomas L. Bohan (57) ABSTRACT

Viewing apparatus for precisely locating and viewing a specific feature or area of the body, particularly in a hard-to-view area. The apparatus includes a viewing device, a general illumination device and a light beam pointer device. The viewing device may be a mirror and/or a camera with monitor. The viewing device is mountable on a freestanding support stand that provides a means for maneuvering the viewing device into a desired position and holding it in that position without the viewing device having to be held in position manually. The light beam pointer device is provided for precisely indicating a specific feature or area reflected in the viewing device, and the general illumination device for illuminating the intended viewing site. The camera and monitor provide a means for viewing a hard-to-view feature or area of the body, particularly on an extremely obese person.

9 Claims, 5 Drawing Sheets

VIEWING APPARATUS

BACKGROUND INFORMATION

1. Field of the Invention

The invention relates to the field of viewing apparatus. More particularly, the invention relates to viewing apparatus that are precisely positionable. More particularly yet, the invention relates to a viewing device mounted on a freestanding base.

2. Description of the Prior Art

Medical or personal care procedures may require that individuals precisely locate or identify a particular area or feature on their bodies in order to perform some procedure on it. Some areas of the body are difficult to view without the aid of a viewing device. The area to be viewed may be intimate and unfamiliar to the individual and the individual may require instruction to properly identify a particular feature. In some cases, it is necessary that another person show or point out the particular feature or area that is of interest. If the area of interest involves the genitals, it may be awkward or embarrassing for the patient if another person has to stand in close proximity to precisely point out a specific feature. For example, when training a woman to self-catheterize, it is often necessary that a nurse point out where exactly the opening to the urinary tract is. In such situations, it is desirable to have a means for illumination and identifying the particular physical feature that allows the instructor to increase the comfort level of the patient by maintaining a physical distance from the person receiving the instruction. Furthermore, it is also desirable to have a means that enables the person receiving the instruction to point to the feature herself in a way that the instructor can verify that she has indeed identified the proper area or feature.

Such a means is a viewing device that is easily adjustable to adequately reflect the intended area. Ideally, the viewing device is freestanding and easily maneuverable into a position to reflect the intended area. It is also important that the hands of the individual remain free to perform tasks, while using the viewing device to view the area. Illumination may be required to provide better visibility of the area.

Prior art discloses mirrors that use a gooseneck type of mechanism for omnidirectional positioning. Several types of mirror are available that are installed on freestanding bases. The bases are usually height adjustable and provide locking mechanisms for adjusting the position of the mirror to provide the desired reflection and for locking the viewing device in that position. Two-sided mirrors with magnification on one side are also known. Some mirrors provide illumination through the use of a light installed in the mirror frame.

Conventional mirrors have disadvantages that make it difficult for a person to use them when it is also necessary to have the hands free to perform certain tasks. None of the conventional mirrors provide a means of precisely locating a particular feature or area of a person's body. Furthermore, a morbidly obese person may not be able to use a conventional mirror to view certain areas of his or her body. In such a case, it may be desirable to have a camera and display that provides an expanded range of viewing. In addition, the conventional lighted mirror has a power cord that presents a safety hazard in that a person can trip over a cord that extends from the mirror across the floor to a power source located in a wall.

What is needed, therefore, is viewing apparatus that is omnidirectionally positionable so as to reflect a particular desired view. What is further needed is such viewing apparatus that is retainable in a particular position without being held manually in that position. What is yet further needed is such viewing apparatus that provides a means to precisely locate an area or feature on a person's body. What is still yet further needed is such viewing apparatus that provides a means for illumination that does not present a safety hazard.

BRIEF SUMMARY OF THE INVENTION

It is an object of the present invention to provide viewing apparatus that is omnidirectionally positionable. It is further an object to provide such apparatus that is retainable in a particular position without being manually held in that position. It is yet further an object to provide such apparatus that provides a means of precisely locating a specific area or feature on the body, particularly at the lower end of the torso. It is still yet further an object to provide such apparatus that is safe to use.

The objects cited above are achieved by providing viewing apparatus that comprises a viewing device mounted on a support stand and an illumination device for illuminating the intended viewing site. The viewing device maybe a mirror and/or a camera with a monitor. The camera may be a video camera. The illumination device may include a general illumination device, i.e. a conventional light source for broad illumination of the intended viewing site, as well as a small-area illumination device, i.e., a light beam pointer device, such as a laser pointing device, for pointing to a particular feature or area of view. Ideally, the various power-consuming devices are cordless.

A key feature of the viewing apparatus according to the invention is that the viewing device is mounted on a freestanding support stand that provides the proper height for viewing the intended viewing site, whereby the intended viewing site may be in the genital area and the person using the viewing apparatus may be seated on a chair or a toilet, may be standing, or may be lying in a bed. Thus, the proper height in some applications of the viewing device may vary between two and three feet from the floor surface, and in other applications may vary between three and four feet from the floor. Also, the viewing device may have to be positioned above the surface of a bed. Depending on the particular venue of use, the support stand may be height-adjustable to accommodate foreseeable variations in the required height of the viewing device, or may be a fixed height for use in a setting with standardized equipment, such as in a clinic or hospital setting.

It is important that the viewing device be very flexible in its positionability and be arrestable in a particular position, so that the person using the viewing device has both hands free to perform other tasks with the aid of the viewing device. There are a number of suitable conventional means of attaching the viewing device to the support stand in a manner that provides the desired omni-positionability of the viewing device and that also allows the viewing device to be arrested in a particular position. For example, the support stand may include a bendable arm or a flexible support commonly referred to as a "gooseneck" that allows the viewing device to be moved along any number of imaginary axes, so as to provide precise positionability of the viewing device, the light source and the light beam pointer device. The mounting end of the gooseneck and the mounting base of the viewing device are equipped with a mating fastening means, whereby any suitable fastening means, such as, mating threaded fasteners, interference or friction-fit assemblies, hole-and-locking-pin assemblies, etc., may be used.

The arm or the gooseneck provides a certain resistance to change of position once it is arrested in a position and thereby holds the position of the device in its arrested position.

A further key feature of the viewing apparatus is that the illumination devices, i.e., the general illumination device and the light beam pointer device, are an integral part of the apparatus and are attached either to the support stand or to the viewing device itself. The general illumination device is positioned to illuminate a broad area that includes the intended viewing site and the light beam pointer device is positioned to directly target a particular feature or small area within the intended viewing site. The illumination devices may be positionable independently of the viewing device, or may be mounted on the viewing device such that their positions are adjusted when the position of the viewing device is adjusted. Various configurations are included within the scope of the invention. For example, the general illumination device may be fixedly attached to the viewing device so as to be positionally adjustable in concert with the viewing device, and the light beam pointer device may be separately mounted and positionable independently of the position of the viewing device and general illumination device, or vice versa. Numerous means for attaching the general illumination device and the light beam pointer device to the support stand are suitable, such as the use of a clamp that is clamped to the freestanding support stand and securely holds the general illumination device and the light beam pointer device. The clamp allows both vertical and horizontal adjustment of the general illumination device and the light beam pointer device. A single clamp may be used to hold both the general illumination device and the light beam pointer device, whereby the direction of illumination of both illumination devices is adjusted during initial set-up of the viewing apparatus and a single adjustment of the clamp re-directs the direction of illumination from both illumination devices. In the alternative, separate clamps may be used to attach the general illumination device and the light beam pointer device individually to the support stand, thereby allowing each illumination device to be positioned independently according to need.

In some situations, it is necessary to use a viewing device to view the genital area in order to perform some procedure, such as self-catheterization. Many types of support stands are known and are suitable for use with the device according to the invention. Important in the construction of the support stand is that it be capable of receiving and securely holding the viewing device and the illumination devices, and of maintaining a specific set position of the devices for at least a period of time that will allow the user to perform a task or procedure with the aid of the viewing device. Depending on the application, the support stand may be a fixed height, or may be height-adjustable.

An example of a conventional support stand is that of a conventional tripod stand, such as is used to securely mount a camera to a tripod. The top of the tripod is equipped with a conventional omnidirectional camera mount of the type used to hold a camera in a particular position. When used with such a support stand, the mounting base of the viewing device is provided with a threaded bore and is threaded onto the conventional male threaded fastener provided on the camera clamp mechanism. The general illumination devices are attached by means of a clamp that provides omnidirectional adjustability. The clamp may be mounted either to a center pole or to one of the legs of the tripod, depending on the design of the tripod. The viewing device is then positionable to illuminate and reflect the intended viewing site and lockable into that position by means of a locking mechanism provided on the conventional camera mount.

Depending on the particular intended venue of use for the viewing apparatus, more rugged types of support stands may be used as the freestanding support stand for the device. For example, for use in a hospital or clinic setting, one type of stand that is suitable for mounting the viewing device is similar to the stand that is used to support intravenous fluids in hospitals. Such a stand has a vertically adjustable center pole on a base of four supports fitted with casters, which may be lockable. The support stand is rugged, hard to tip over, and easily movable from one location to another. This type of conventional support stand is adapted to receive the viewing device and to provide the proper height for the intended viewing site. For example, the hook support for the intravenous fluid bags is replaced with a gooseneck flexible arm or with another suitable type of joint, such as a gimbal mechanism that is adapted to receive and retain the viewing device and that provides the desired omnidirectional positioning of the viewing device. The center pole may be height-adjustable or of a fixed height.

The viewing apparatus according to the invention is also suitable for use by a person who is bed-ridden and needs to view an area of the body that is inaccessible to view by the person, who consequently requires the use of a viewing device. For such applications, the viewing device is best supported on a support stand that has a horizontal arm that is adjustable in length, so that the viewing device is maneuverable into a position that is over the surface of a bed.

The viewing device that is mounted on the support stand may be a single-sided mirror or a double-sided mirror, with one side having a magnification factor greater than one. A typical mirror magnification factor for the purposes of training a person to do self-catheterization has proven to be a factor of 2×. The ideal magnification factor depends, of course, on the intended application of the device. The magnification mirror is located opposite the conventional mirror side and the two mirrors provide the front and rear surfaces of the viewing device, respectively.

In an alternative embodiment of the present invention, the viewing device is a video camera, analog or digital, with monitor. This embodiment of the invention is particularly useful in enabling an extremely obese person to view an otherwise visually inaccessible area of the body, such as the genital area. The camera is attached to the support stand in a manner similar to that of the general illumination device and the light beam pointer device. The camera may be mounted on the support stand as well, but may also be mounted instead separately from the support stand, to as to provide convenient and unencumbered viewing by the user of the apparatus. The camera is positionable to view the intended viewing site and sends a live image of the intended viewing site to the monitor for the person to view. The monitor may also provide a larger viewing area than a conventional mirror.

In still another embodiment of the invention, the viewing device comprises a mirror assembled in a housing that includes an assembly for the illumination devices. For example, the general illumination device is mounted within the housing so as to project a relatively broad beam of light toward the intended viewing site. An aperture is provided in the housing or in the surface of the mirror through which the beam of light from the light beam pointer device is projected outward toward the intended viewing site. The housing may be constructed to enclose a battery pack between the front and rear surfaces of the viewing device that serves as a power source for both the general illumination device and the light beam pointer device, or an external battery pack may be provided that is mounted on the support stand and connects to the illumination devices.

Similarly, another embodiment of the viewing device comprises a mirror assembly that incorporates a camera with the lens assembled in the housing behind an aperture that is provided in the housing or in the mirror surface and a monitor mounted on the support stand. The camera transmits the image of the intended viewing site and sends the image to the monitor, thereby enabling a person to view the site.

The viewing apparatus according to the invention includes at least one power source that provides power for the viewing device and the general illumination devices. The power source may include a power cord that plugs into a conventional power outlet and provides 120 V AC or 12 V DC voltage and/or a battery pack. Ideally, particularly in a clinic or hospital setting, batteries rather than a power cord are used, to avoid the hazards presented by a cord extending across the floor. Conventional batteries may be used, as well as rechargeable or solar-chargeable batteries. The viewing device, the general illumination device, and the light beam pointer device may each be equipped with an independent battery source. Alternatively, a single battery pack may be used to provide power to the viewing device as necessary, the general illumination device and the light beam pointer device, or to any combination of devices. A power cable for use in recharging the rechargeable batteries may also be stored within the housing for connecting the rechargeable battery unit to a conventional AC voltage power source as needed.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE INVENTION

Figure 1:
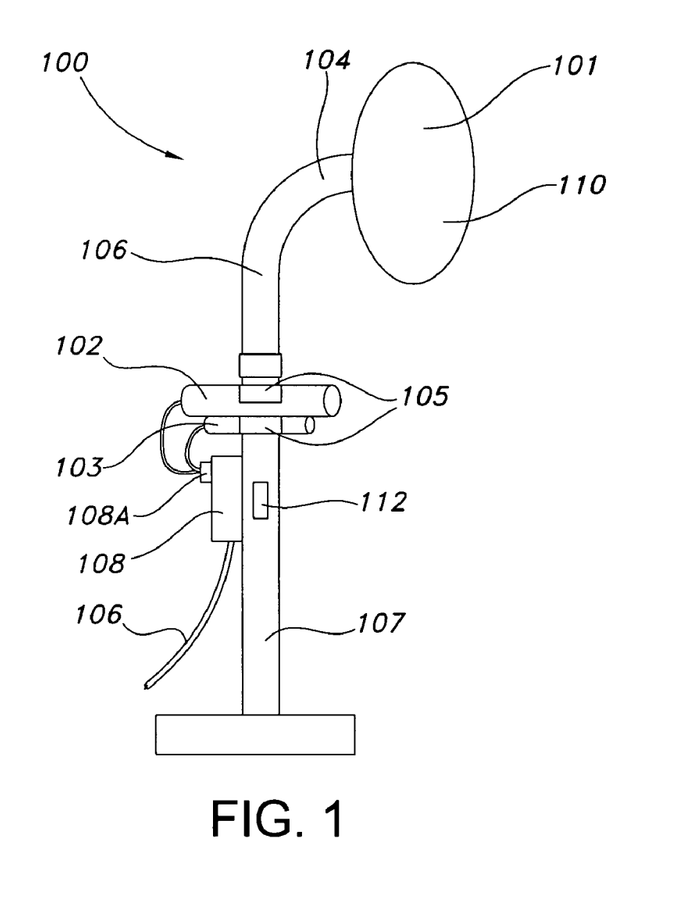
FIG. 1 is an elevational view of the first embodiment of the viewing apparatus according to the invention, wherein the viewing device comprises a mirror.

FIG. 1 illustrates a first embodiment of the viewing apparatus 100 according to the invention. The viewing apparatus 100 comprises a mirror 101 as a viewing device 110 and at least one general illumination device 102 for illuminating an intended viewing site. With certain applications, it may be desirable to include a narrow-beam illumination device, such as a light beam pointing device 103, for use in pointing to a particular feature or area within the intended viewing site. The general illumination device 102 may be any suitable source, such as a light bulb or a flashlight. In the embodiment described, the light beam pointer device 103 is a conventional laser diode. It should be understood, that various types of illumination are included within the scope of the invention. For example, an incandescent, fluorescent, or halogen light bulb is a suitable and acceptable general illumination device. The light beam pointer device 103 is also not limited to a laser beam; rather, other types of illumination devices that provide a beam of light with very little scattered light so that the beam functions well as a pointer are also suitable and acceptable. Ideally, each of the illumination devices 102, 103 is a battery-operated device having its own housing and assembly for receiving the batteries. The mirror 101 is adjustably mounted on a support stand 107 by a mounting bracket 104. The general illumination device 102 and the light beam pointer device 103 are held in a clamp 105 that is fixedly attached to the support stand 107. As shown here, the clamp 105 holds both the general illumination device 102 and the light beam pointer device 103. It is, of course, also within the scope of the invention to to use individual clamps 705B, 705C to clamp the devices 102, 103 to the support stand 107, independently of each other, as shown below in FIG. 7. In this embodiment, a battery pack 108 is mounted on the support stand 107 and provides power to the illumination devices 102, 103. A cable 106 is provided for recharging the batteries.

Figure 2:
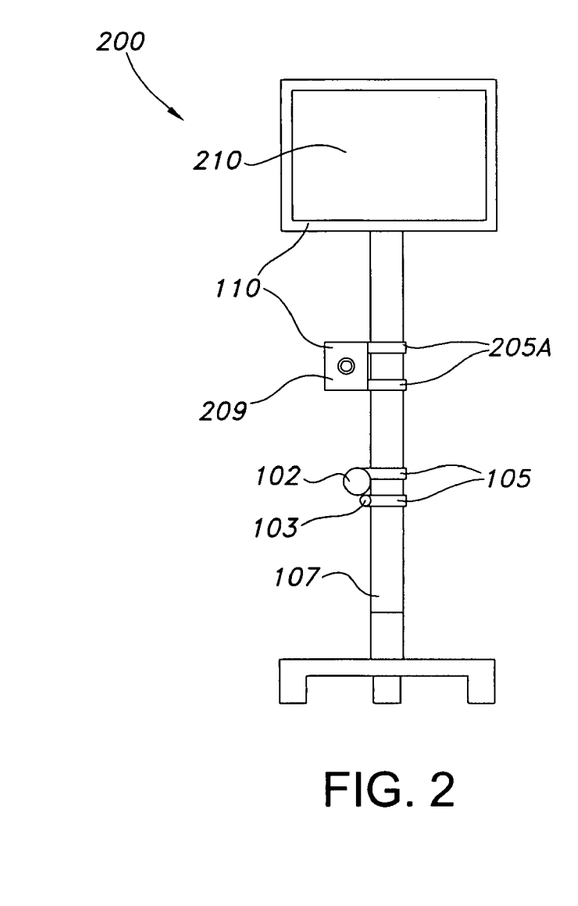
FIG. 2 is an elevational view of the second embodiment of the viewing apparatus according to the invention, wherein the viewing device comprises a camera and display.

FIG. 2 illustrates the second embodiment of the viewing apparatus 200 according to the invention, which uses a camera 209 and a monitor 210 as the viewing device 110. The monitor 210 is mounted on the support stand 107 and positionable to provide easy viewing by the user. It is also within the scope of the invention to place the monitor on a separate mount, if necessary, to provide more comfortable viewing. A camera clamp 205A is used to mount the camera 209 on the support stand 107 and the clamp 105 to mount the general illumination device 102 and the light beam pointer device 103. The camera 209 is positionable to allow viewing of the intended viewing site. A live image of the intended viewing site is sent to the monitor 210 through a cable 309A (shown in FIG. 3) that connects the camera 209 to the monitor 210. Ideally, the camera 209 and the monitor 210 have an independent power source, such as a battery pack.

Figure 3:
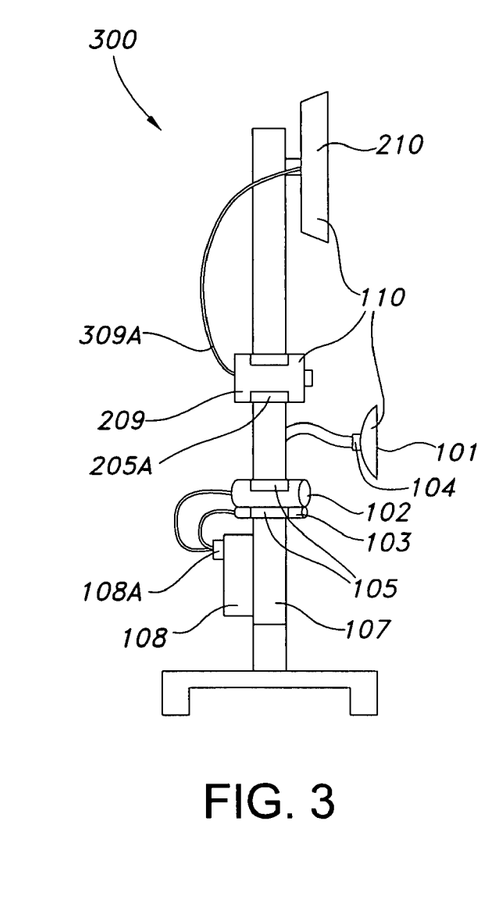
FIG. 3 is an elevational view of the third embodiment of the viewing apparatus according to the invention, wherein the viewing device includes the camera and display of FIG. 2 and the mirror of FIG. 1.

FIG. 3 illustrates the third embodiment of the viewing apparatus 300. In this embodiment, the mirror 101 is mounted as an auxiliary viewing device on the support stand 107, in addition to the camera 209 and the monitor 210 shown in FIG. 2.

Figure 4:
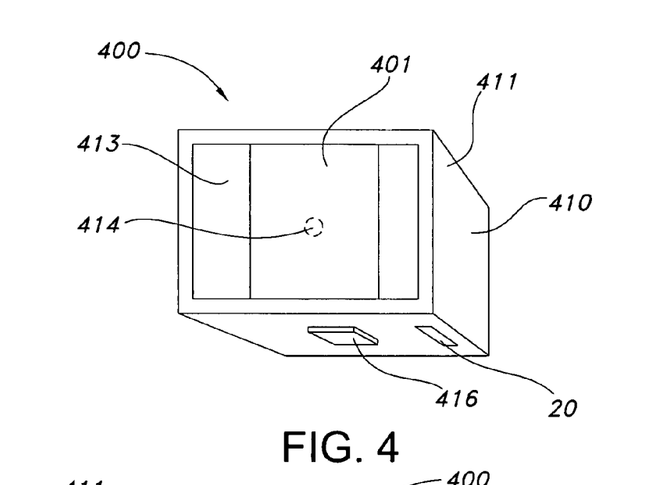
FIG. 4 is a perspective view of the fourth embodiment of the viewing apparatus according to the invention, comprising a general illumination device and a light pointer beam device integrated into the housing, with the light beam emitting from the front face of the viewing device, and showing the mounting plate on the bottom face.
Figure 5:
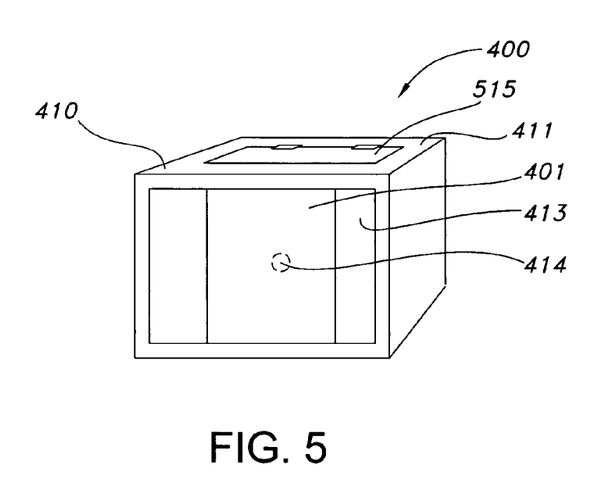
FIG. 5 is a perspective view of the viewing apparatus of FIG. 4, showing the access panel for accessing the internal assemblies of the viewing device.
Figure 6:
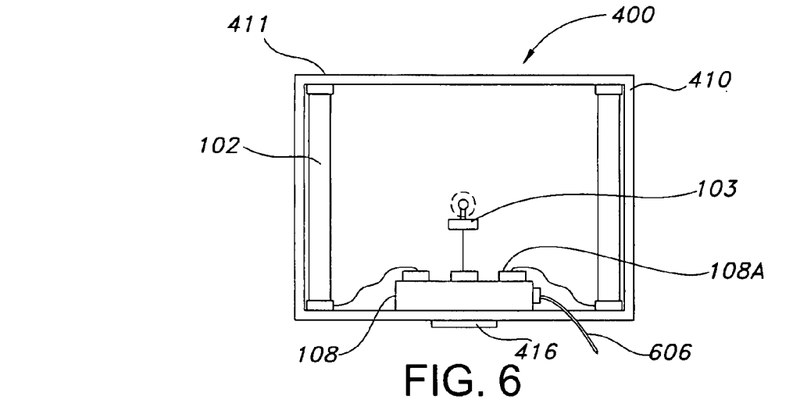
FIG. 6 is an elevational view of the rear face of the viewing device of FIG. 4, with the rear wall of the housing removed, showing the general illumination device, the light beam pointer device, and a battery pack.

FIGS. 4–6 illustrate the fourth embodiment of the viewing apparatus 400 according to the invention. The viewing apparatus 400 comprises a viewing device 410 that is mounted on the support stand 107. The support stand 107 is any one of the stands shown in FIGS. 1–3 and 7–9 and is not shown here. The viewing device 410 comprises a double-faced mirror 401, a general illumination device 102, and a light beam pointer device 103, all of which are contained within a housing 411. The mirror 401 has a beam-emitting window 414 through which a beam of laser light is emitted when the light beam pointer device 103 is actuated. The beam-emitting window 414 is shown incorporated into the surface of the mirror 401. It should be understood, however, that the purpose of the beam-emitting window 414 is that it direct a beam of light to a particular area within the area reflected in the mirror 401 and that it may be incorporated into the housing 411, rather than into the mirror 401. FIG. 5 shows an access panel 515 for accessing the internal area of the housing 411.

The double-faced mirror 401 has a front face that is a simple mirror and a rear face that is a mirror with a magnification factor of 2×. The simple mirror and the magnification mirror appear identical in construction with regard to shape, each also having a beam-emitting window 414. Thus, the front face and the rear face of the double-faced mirror 401 appear identical and are not shown separately.

FIGS. 4 and 6 show a mounting plate 416 that is attached to the housing 411 and which is used to mount the viewing device 410 onto the support stand 107. In the embodiment shown, the mounting plate 416 has a threaded bore that attaches to male threaded fastener that extends from the support stand 107. This mounting plate 416 is by way of illustration only. Other means of mounting the viewing device 410 to the support stand 107 have been described above and are included with the scope of the invention.

Figure 7:
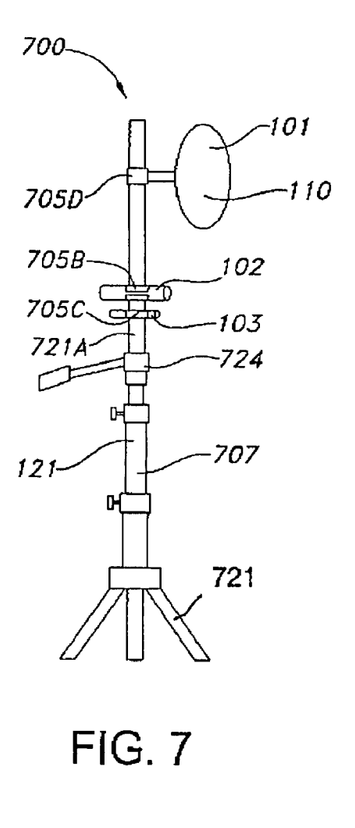
FIG. 7 is an elevational view of the viewing apparatus of FIG. 1 with the viewing device mounted on a standard tri-pod.

FIG. 7 shows a first variation 700 of the first embodiment of the viewing apparatus 100, comprising the viewing device 110, general illumination device 102 and the light beam pointer device 103, all mounted on a tripod support stand 707, which, in this variation is a conventional height-adjustable camera tripod 721. The tripod 721 has a telescoping pole 721A that provides height adjustability. The tripod 721 is equipped with a conventional camera mount 724 with a male threaded fastener. The lower end of the telescoping arm has a mating female threaded fastener and is threaded onto camera mount 724. The camera mount 724 securely holds the telescoping arm 721A on the tripod and allows it to be tilted forward, backward, and sideways, and tightened into a particular position. The clamps 705B, 705C, 705D attach to the telescoping arm 721A and securely hold the general illumination device 102, the light beam pointer device 103 and the viewing device 110, respectively, allowing independent, omnidirectional positioning of the three devices 110, 102, 103.

Figure 8:
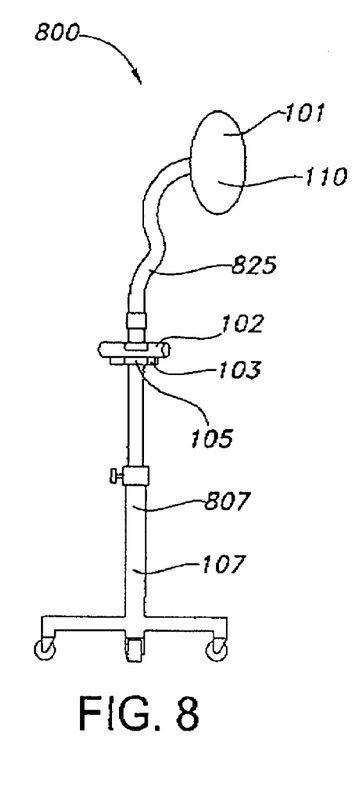
FIG. 8 an elevational view of the viewing apparatus of FIG. 1, showing the viewing device mounted on a rollable support stand.

FIG. 8 shows a second variation 800 of the first embodiment of the viewing apparatus 100, mounted on the support stand 107, which, in this variation, is a height-adjustable support stand 807 with a flexible arm 825. The flexible arm 825 may be a gooseneck type of stiffly flexible conduit with a male threaded post at the top. The viewing device 110 is screwed onto the flexible arm 825 and is then positionable along any number of imaginary axes. The flexible arm 825 requires a certain amount of force to change its position, so that, when the viewing device 110 is mounted on the flexible arm 825 and maneuvered into a particular position, it remains in that position until the required force is applied to the flexible arm 825 to force a change in the position. The clamp 105 attaches to the height-adjustable support stand 807 and secures the general illumination device 102 and the light beam pointer device 103 and allows omnidirectional positioning of the illumination devices 102, 103, together as a single unit. The support stand 807 is ideally fitted with casters on its feet so that it is easily movable from one location to another. Ideally, the casters are lockable to secure the position of the support stand 807.

Figure 9:
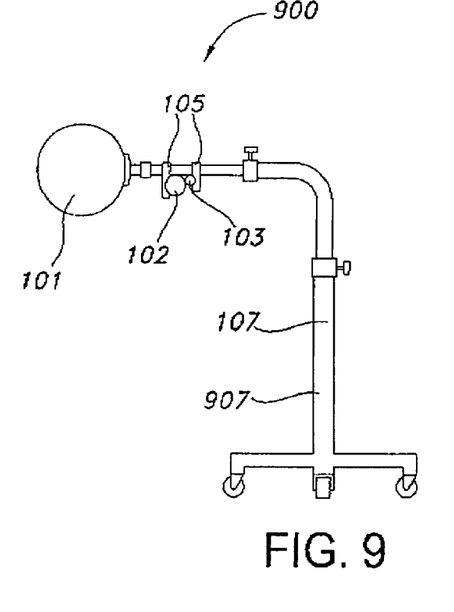
FIG. 9 is an elevational view of the viewing apparatus of FIG. 1, showing the viewing device mounted on a horizontal-reach support stand.

FIG. 9 illustrates a third variation 900 of the first embodiment of the viewing apparatus 100 according to the invention. The viewing device 110 is mounted on the support stand 107, which, in this variation is a horizontal-reach support stand 907. The combination of the viewing device 110 and the horizontal-reach support stand 907 allow a person who is bed-ridden to use the viewing apparatus 100 to view areas of the body that are hard to view, particularly the genital area. As shown, the horizontal portion of the horizontal-reach support stand 907 is adjustable in length. The clamp 105 attaches to the horizontal portion of the horizontal-reach support stand 907 and securely holds the general illumination device 102 and the light beam pointer device 103 in a manner that allows omnidirectional positioning of the devices 102, 103 as one device.

Figures 10, 11, 12:
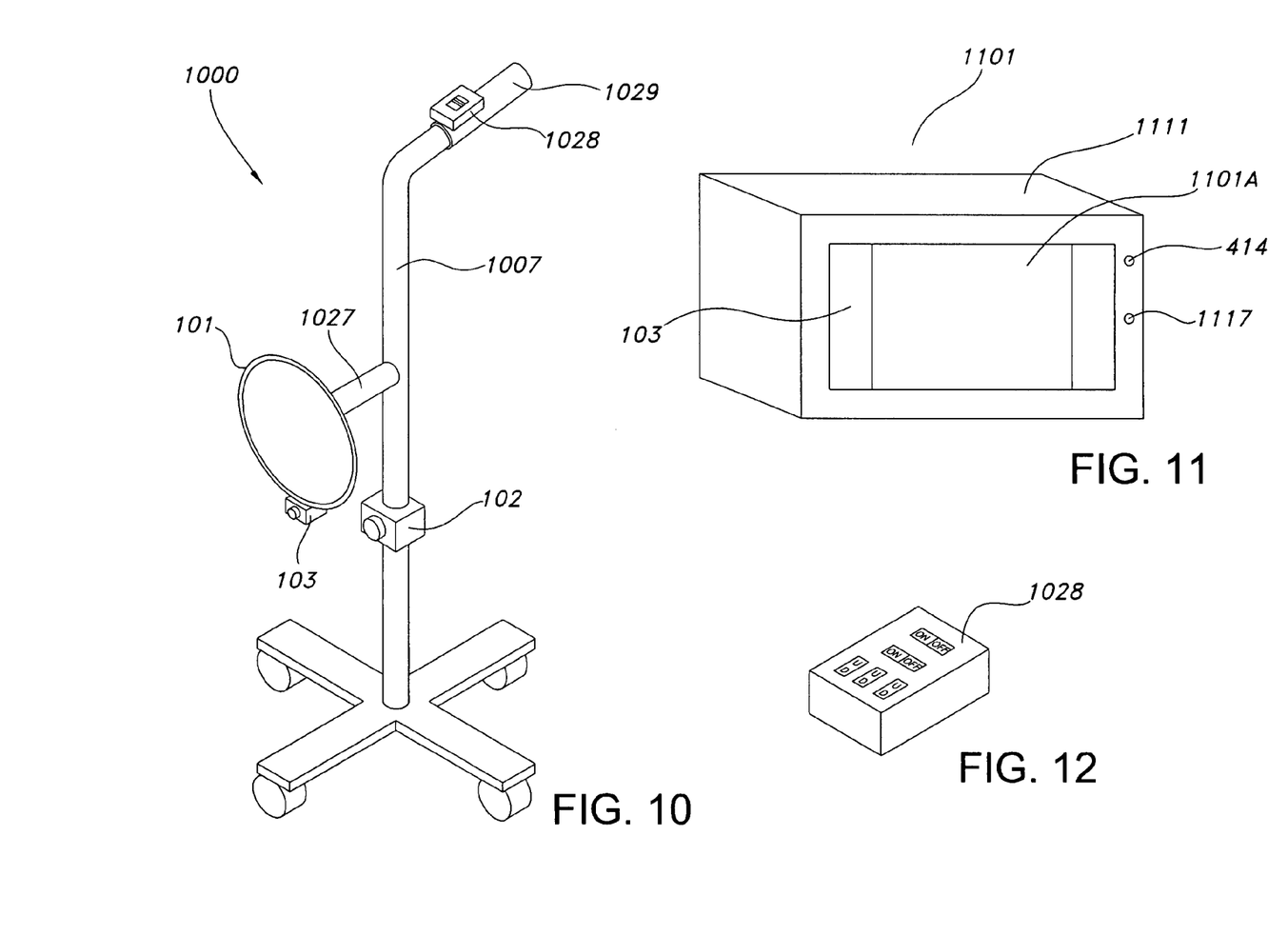
FIG. 10 is an elevational view of the fifth embodiment of the viewing apparatus according to the invention, showing the viewing device and a control module mounted on a rollable support stand.
FIG. 11 is a perspective view of a sixth embodiment of the viewing device, which comprises a mirror with a camera lens integrated into the mirror housing.
FIG. 12 is an illustration of the control module, showing on/off switches and a vertical orientation switch for the light beam pointer device.

FIG. 10 illustrates a fourth variation 1000 of the first embodiment of the viewing apparatus 100 according to the invention. The viewing device 110 is mounted on the support stand 107, which, in this variation, is a fixed-height support stand 1007. In the embodiment shown, the viewing device 110 is mounted on an arm 1027 that extends from the support stand 1007, which, in this variation, is rollable and has a handle 1029 that allows the viewing apparatus to be easily maneuvered into a desirable position. The light beam pointer device 103 is mounted to the viewing device 110 and the general illumination device 102 is mounted on the support stand 1007. A control unit 1028 is mounted on the support stand 1007 to provide a single-source control mechanism for power to the general illumination device 102 and the light beam pointer device 103. The control unit 1028 also provides an orientation control for positioning of the light beam pointer device 103. This allows for an attendant to easily adjust the light beam pointer device 103 from a distance, thereby providing a greater sense of ease and comfort for the patient. Since the lateral position of the illumination on the intended viewing site is easily adjustable by moving the support stand 1007 to the right of the left, the control unit 1028 need only control the vertical orientation of the light beam pointer device 103 or the general illumination device 102. Thus, the control unit 1028 (shown in FIG. 12) has ON/OFF switches to control power to the illumination devices 102, 103 and a UP/DOWN switches to control the vertical orientation of the light beam pointer device 103, the viewing device 110, and/or the general illumination device 102.

It is understood that the viewing device 110 referred to in FIGS. 7–10 may be the mirror 101, the camera 209 with the monitor 210, or a camera-mirror combination as shown in FIG. 3.

As depicted in FIGS. 7–9, the general illumination device 102 and the light beam pointer device 103 may be independently powered. Similarly, the camera 209 and monitor 210, in FIGS. 2 and 3, may be independently powered. Alternatively, FIG. 1 shows a single battery pack 108 mounted on the support stand 107 providing power to the devices 102, 103. The battery pack 108 includes a rechargeable battery and a power cord 606 (shown in FIG. 6) for recharging the rechargeable battery. Also provided with the battery pack 108 are connectors 108A for connecting the general illumination device 102 and the light beam pointer device 103 to the battery. It is, of course, possible to use conventional batteries to power the general illumination device 102 and the light beam pointer device 103, as well as to use a conventional power cable and plug the viewing apparatus 100 into an external power source (not shown). An ON/OFF switch 112 is provided on the support stand 107, with which to turn the general illumination device 102 and the light beam pointer device 103 on or off. FIG. 10 shows a control unit 1028 provided on the support stand 1007, with which to control the power and vertical orientation of the general illumination device 102 and the light beam pointer device 103.

FIG. 11 illustrates a combination viewing device 1101 that comprises a housing 1111 that incorporates a mirror 1101A with a lens aperture 1117 and the camera 209 (not shown). Ideally, the angle of the lens is adjusted during the initial set-up of the combination viewing device 1101 such that the camera 209 transmits substantially the area reflected in the mirror 1101A. It is possible and within the scope of this invention to incorporate the previously described general illumination device 102 and/or the light beam pointer device 103 into the combination viewing device 1101, similarly to that described with reference to FIGS. 4–6. In the embodiment shown in FIG. 11, the lens aperture 1117 and the beam-emitting window 414 are incorporated into the housing 1111, rather than into the surface of the mirror 1101A.

The embodiments of the invention mentioned herein are merely illustrative of the present invention. It should be understood that one skilled in the art will contemplate numerous variations in the construction of the present invention without straying from the intended scope and field of the invention herein disclosed and as claimed.

What is claimed is:

1. Viewing apparatus comprising:
   a viewing device;
   a support stand; and
   a light-beam pointer device that emits a laser beam;
   wherein said viewing device is mounted on said support stand with means for providing omnidirectional positionability of said viewing device and said laser beam from said light beam pointer device illuminates a spot within an area reflected in said viewing device.

2. The viewing apparatus of claim 1, wherein said viewing device is a mirror.

3. The viewing apparatus of claim 1 further comprising a control module that provides an orientation control of said light beam pointer device.

4. The viewing apparatus of claim 3, wherein said control module includes an ON/OFF switch for switching power to said light beam pointer device on or off.

5. The viewing apparatus of claim 1 further comprising a general illumination device mounted on said support stand for providing general illumination in a direction forward of said viewing device, and a control module that provides an ON/OFF switch for switching power to said general illumination device.

6. The viewing apparatus of claim 1, wherein said light-beam pointer device is adjustable in orientation independent of an orientation of said viewing device.

7. Viewing apparatus comprising:
   a viewing device;
   a support stand;
   a light-beam pointer device; and
   a control module that provides an orientation control of said light beam pointer device;
   wherein said viewing device is mounted on said support stand with means for providing omnidirectional positionability of said viewing device and said light beam pointer device is mounted such that a beam emitted from said light beam pointer device illuminates a spot within an area reflected in said viewing device.

8. Viewing apparatus comprising:
   a viewing device;
   a light beam pointer device; and
   a control module;
   wherein said light beam pointer device is mounted on said viewing device and wherein said control module provides an orientation control of said light beam pointer device.

9. The viewing apparatus of claim 8, wherein said control module provides an ON/OFF switch for switching power to said light beam pointer device on or off.

* * * * *